(12) United States Patent
Lydecker et al.

(10) Patent No.: US 11,878,092 B2
(45) Date of Patent: Jan. 23, 2024

(54) MEDICAL COMPOSITIONS BASED ON CROSSLINKABLE HYDROPHILIC POLYMERS

(71) Applicant: Boston Scientific Scimed Inc., Maple Grove, MN (US)

(72) Inventors: Lauren Lydecker, Millbury, MA (US); Jennifer Whelehan, Westborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 588 days.

(21) Appl. No.: 16/999,856

(22) Filed: Aug. 21, 2020

(65) Prior Publication Data

US 2021/0060211 A1 Mar. 4, 2021

Related U.S. Application Data

(60) Provisional application No. 62/892,796, filed on Aug. 28, 2019.

(51) Int. Cl.
*A61L 27/52* (2006.01)
*A61L 27/58* (2006.01)
(Continued)

(52) U.S. Cl.
CPC ............... *A61L 27/52* (2013.01); *A61L 27/58* (2013.01); *C08J 3/24* (2013.01); *C08L 5/08* (2013.01); *C08L 101/005* (2013.01)

(58) Field of Classification Search
CPC .................................... A61L 27/52; C08L 5/08
See application file for complete search history.

(56) References Cited

U.S. PATENT DOCUMENTS 6,818,018 B1 11/2004 Sawhney
8,383,161 B2 2/2013 Campbell et al.
(Continued)

FOREIGN PATENT DOCUMENTS

EP 065621 A1 * 6/1995
EP 0656215 A1 6/1995
(Continued)

OTHER PUBLICATIONS

International Search Report and Written Opinion for the International Patent Application No. PCT/US2020/047443, dated Nov. 30, 2020, 19 pages.
(Continued)

*Primary Examiner* — Carlos A Azpuru
(74) *Attorney, Agent, or Firm* — Seager, Tufte & Wickhem, LLP

(57) ABSTRACT

In accordance with some aspects, the present disclosure is directed to medical compositions that comprises (a) a first hydrophilic polymer functionalized with a plurality of first functional groups and (b) a second hydrophilic polymer functionalized with a plurality of second functional groups, wherein the first and second functional groups are selected to react and form covalent bonds upon a change in conditions such that the first and second hydrophilic polymers crosslink with one another. In other aspects the present disclosure is directed to kits that comprise such medical compositions and to medical procedures that utilize such medical compositions.

9 Claims, 1 Drawing Sheet

(51) Int. Cl.
 *C08J 3/24* (2006.01)
 *C08L 5/08* (2006.01)
 *C08L 101/00* (2006.01)

(56) References Cited

U.S. PATENT DOCUMENTS

| | | |
|---|---|---|
| 9,510,810 B2 | 12/2016 | Ladet et al. |
| 2011/0142936 A1 | 6/2011 | Campbell et al. |

FOREIGN PATENT DOCUMENTS

| | | | |
|---|---|---|---|
| WO | 0012018 A1 | | 3/2000 |
| WO | WO 00/12018 A1 | * | 3/2000 |
| WO | 2010/134988 A1 | * | 11/2010 |
| WO | 2010134988 A1 | | 11/2010 |

OTHER PUBLICATIONS

"Augmenix Announces Positive Three-year SpaceOAR Clinical Trial Results," Imaging Technology News, Oct. 27, 2016.
"Augmenix Receives FDA Clearance to Market its TraceIT™ Tissue Marker," BusinessWire Jan. 28, 2013.

* cited by examiner

MEDICAL COMPOSITIONS BASED ON CROSSLINKABLE HYDROPHILIC POLYMERS

CROSS-REFERENCE TO RELATED APPLICATION

This application claims the benefit of U.S. Provisional Application No. 62/892,796, entitled "MEDICAL COMPOSITIONS BASED ON CROSSLINKABLE HYDROPHILIC POLYMERS" and filed Aug. 28, 2019, the entire disclosure of which is incorporated herein by reference.

FIELD

The present disclosure relates to medical compositions based on crosslinkable hydrophilic polymers, as well as to kits containing such compositions, methods of making such compositions, and methods of using such compositions, among other aspects. The medical compositions of the present disclosure are useful, for example, in the formation of protective barriers over tissue.

BACKGROUND

Current endoscopic procedures such as endomucosal resection (EMR), endosubmucosal dissection (ESD), anastomosis, fistula creation (formed intentionally or of disease origin), inflammatory bowel disease (IBD), and IBD subsidiary diseases all result in damage to gastrointestinal (GI) tissues and often leave very thin layers of GI tract wall.

Currently there is a need for a suitable technology that provides a barrier for post-surgical and post-disease protection and healing. In this regard, endoscopists currently rely on surgical procedures, including clipping, or endoscopic suturing to appose tissue and allow healing. These procedures, however, are frequently not suitable for large defects, friable tissue, or fibrotic tissue. Moreover, complications that can arise from the absence of a protective barrier include, but are not limited to, perforation, infection, and sepsis.

SUMMARY OF THE INVENTION

In accordance with some aspects, a medical composition is provided that comprises (a) a first hydrophilic polymer functionalized with a plurality of first functional groups and (b) a second hydrophilic polymer functionalized with a plurality of second functional groups, wherein the first and second functional groups are selected to react and form covalent bonds upon a change in conditions such that the first and second hydrophilic polymers crosslink with one another.

In some embodiments, the medical composition may be a first composition that comprises a mixture of the first and second hydrophilic polymers, and the change in conditions may be a change in pH. For example, the first and second hydrophilic polymers may crosslink with one another when a pH of an environment surrounding the mixture of the first and second hydrophilic polymers achieves a pH value ranging from 7 to 9, among others values.

In some embodiments, which may be used in conjunction with any of the above aspects and embodiments, the first and second hydrophilic polymers crosslink with one another at a rate such that the mixture becomes a non-free-flowing gel in less than 10 minutes, preferably less than 5 minutes, at body temperature.

In some embodiments, which may be used in conjunction with any of the above aspects and embodiments, the first and second functional groups are selected to react and form covalent bonds via a click chemistry reaction mechanism.

In some embodiments, which may be used in conjunction with any of the above aspects and embodiments, the first functional groups comprise succinimidyl groups and the second functional groups comprise primary amine groups. In some of these embodiments, the succinimidyl groups may be linked to the first hydrophilic polymer by a hydrolysable linkages.

In some embodiments, which may be used in conjunction with any of the above aspects and embodiments, (a) the first hydrophilic polymer may be a multi-arm hydrophilic synthetic polymer having arms that comprise the succinimidyl groups, (b) the second hydrophilic polymer may be chitosan, or (c) the first hydrophilic polymer may be a multi-arm hydrophilic synthetic polymer having arms that comprise the succinimidyl groups and the second hydrophilic polymer may be chitosan.

In some embodiments, which may be used in conjunction with any of the above aspects and embodiments, the medical composition may further comprise an additional agent selected from therapeutic agents and radiological agents.

In some aspects, the present disclosure provides a kit for forming a protective barrier on bodily tissue. The kit comprises (a) a first hydrophilic polymer functionalized with a plurality of first functional groups and (b) a second hydrophilic polymer functionalized with a plurality of second functional groups, wherein the first and second functional groups are selected to react and form covalent bonds upon a change in conditions such that the first and second hydrophilic polymers crosslink with one another.

In some embodiments, the kit comprises a first reservoir containing the first and second hydrophilic polymers.

In some embodiments, the kit comprises a first reservoir containing the first hydrophilic polymer and a second reservoir containing the second hydrophilic polymer.

In some embodiments, which may be used in conjunction with any of the above aspects and embodiments, the change in conditions is a change in pH and the first and second functional groups react and form covalent bonds when a pH of an environment surrounding a mixture of the first and second hydrophilic polymers is changed from a first pH value to a second pH value that differs from the first pH value.

In some embodiments, which may be used in conjunction with any of the above aspects and embodiments, the kit may comprise (a) a first reservoir containing a first free-flowing liquid composition having the first pH and comprising the first and second hydrophilic polymers, (b) a first reservoir containing a free flowing dry composition that comprises the first and second hydrophilic polymers and may be adapted to form a first free-flowing liquid composition having the first pH and comprising the first and second hydrophilic polymers upon addition of a suitable diluent, (c) a first reservoir containing a free flowing dry composition that comprises the first hydrophilic polymer and a second reservoir containing a free flowing liquid composition that comprises the second hydrophilic polymer, wherein when mixed, contents of the first and second reservoirs form a first free-flowing liquid composition having the first pH and comprising the first and second hydrophilic polymers, or (d) a first reservoir containing a first free-flowing dry composition comprising the first and second hydrophilic polymers that is adapted to be propelled as a dry composition onto tissue.

In some embodiments, which may be used in conjunction with any of the above aspects and embodiments, the kit further comprises an additional reservoir containing (a) a second free-flowing liquid composition or (b) a powder that is configured to form a second free-flowing liquid composition upon addition of a suitable diluent. For example, the second free-flowing liquid composition may be a buffer solution. In addition, upon combining the second free-flowing liquid composition with the first free-flowing liquid composition in a ratio within a range of from 1:10 to 10:1, a mixture may be formed having the second pH value.

In some embodiments, which may be used in conjunction with any of the above aspects and embodiments, the first and second functional groups are selected to react and form covalent bonds via a click chemistry reaction mechanism.

In some embodiments, which may be used in conjunction with any of the above aspects and embodiments, the first functional groups comprise succinimidyl groups, the second functional groups comprise primary amine groups, the first pH value ranges from 4 to 5, and the second pH value ranges from 9 to 10.

In some embodiments, which may be used in conjunction with any of the above aspects and embodiments, the kit further comprises a delivery device configured to deliver the first and second hydrophilic polymers to a site of the bodily tissue.

In some aspects, the present disclosure pertains to a medical procedure for providing a protective barrier on bodily tissue comprising applying the following compositions to tissue: (a) a first composition that comprises a first hydrophilic polymer functionalized with a plurality of first functional groups and a second hydrophilic polymer functionalized with a plurality of second functional groups, wherein the first and second functional groups are selected to react and form covalent bonds upon a change in conditions such that the first and second hydrophilic polymers crosslink with one another and (b) a second composition that is a free-flowing liquid composition, wherein the first free-flowing composition and the second free-flowing liquid composition are applied such that the change in conditions occurs.

In some embodiments, the first composition may be a free-flowing dry composition comprising the first and second hydrophilic polymers.

In some embodiments, the first composition may be a free-flowing liquid composition comprising the first and second hydrophilic polymers.

In some embodiments, the first composition is a first free-flowing liquid composition that has a first pH value, the first and second functional groups react and form covalent bonds upon a change in pH such that the first and second hydrophilic polymers crosslink with one another, and the first and second compositions are applied such that a mixture is be formed having second pH value differing from the first pH value and such that crosslinking between the first and second hydrophilic polymers occurs at a rate such that the mixture quickly becomes a non-free-flowing gel (e.g., in less than 10 minutes).

In some embodiments, which may be used in conjunction with any of the above aspects and embodiments, the first and second compositions are applied to the tissue independently.

In some embodiments, which may be used in conjunction with any of the above aspects and embodiments, the first and second compositions are mixed and applied to the tissue.

In some embodiments, which may be used in conjunction with any of the above aspects and embodiments, first composition is a free-flowing liquid composition and the first and second compositions are applied in a ratio within a range of from 10:1 to 1:10.

In some embodiments, which may be used in conjunction with any of the above aspects and embodiments, the first and second functional groups are selected to react and form covalent bonds via a click chemistry reaction mechanism.

In some embodiments, which may be used in conjunction with any of the above aspects and embodiments, the first functional groups comprise succinimidyl groups, the second functional groups comprise primary amine groups, the first pH value ranges from 4 to 5, and the second pH value ranges from 9 to 10.

In some embodiments, which may be used in conjunction with any of the above aspects and embodiments, (a) the first hydrophilic polymer is a multi-arm hydrophilic synthetic polymer that comprises the succinimidyl groups, (b) the second hydrophilic polymer is chitosan, or (c) the first hydrophilic polymer is a multi-arm hydrophilic synthetic polymer that comprises the succinimidyl groups and the second hydrophilic polymer is chitosan.

In some embodiments, which may be used in conjunction with any of the above aspects and embodiments, the bodily tissue may be GI tissue.

In some embodiments, which may be used in conjunction with any of the above aspects and embodiments, the first and second compositions are applied endoscopically.

In some embodiments, which may be used in conjunction with any of the above aspects and embodiments, the first composition and the second composition are admixed with one another in a delivery device prior to contacting the bodily tissue.

The above and other aspects and embodiments of the present disclosure will become readily apparent to those of ordinary skill in the art upon review of the Detailed Description to follow.

DETAILED DESCRIPTION

Figure 1:
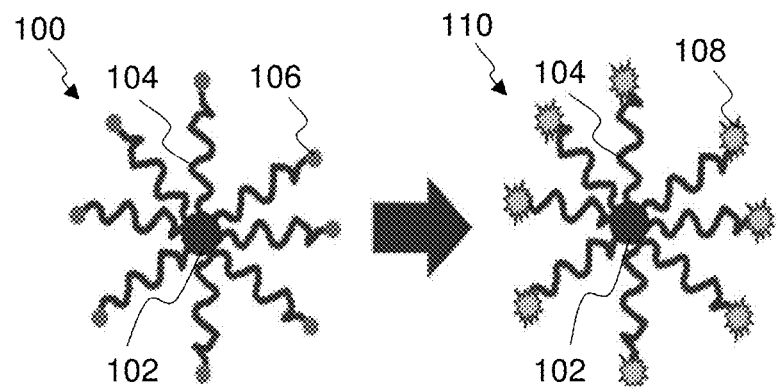
FIG. 1 is a schematic illustration of a method of making a hydrophilic polymer that is functionalized with a plurality of reactive functional groups, in accordance with an embodiment of the present disclosure.

The present disclosure provides compositions that are useful in providing protective tissue barriers, among various other uses.

In various aspects, the present disclosure pertains to medical compositions that comprises a first hydrophilic polymer and a second hydrophilic polymer, which compositions crosslink upon a change in conditions, including a change in pH.

The first and second hydrophilic polymers may be selected from natural hydrophilic polymers, synthetic hydrophilic polymers, and combinations of the same. Examples of natural hydrophilic polymers includes polysaccharides, polypeptides and proteins, including glycoproteins. Particular examples include, for example, chitosan, glycosarninogiycans (e.g., chitin, hyaluronan, chondroitin, dermatan, heparin/heparan, heparosan, keratan, etc.), polylysine, alginic add, various gums including guar gum, fenugreek gum, tara gum, locust bean gum, carob gum, amylopectin, gum arabic, arabinoxylan, xanthan gum, starch, dextranomer, gelatin, collagen, fibrin, fibrinogen, and elastin, among others. Examples of synthetic hydrophilic polymers include poly(alkylene oxides), such as poly(ethylene oxide) (also referred to as polyethylene glycol (PEG)), poly(propylene oxide) or poly(ethylene oxide-co-propylene oxide), poly(vinylpyrrolidone) (PVP), poly(vinyl alcohol), poly(allyl alcohol), poly(ethyleneimine), poly(allylamine), poly(vinyl amine), polyacrylamide, poly(hydroxyethyl methacrylate) (PHEMA), polyoxazolines including poly(2-alkyl-2-oxazolines) such as poly(2-methyl-2-oxazoline), poly(2-ethyl-2-oxazoline) and poly(2-propyl-2-oxazoline), among others. Mixtures of any of the preceding may be employed. It is noted that, due to their hydrophilicity, many of these polymers may exhibit mucoadhesive properties. Many of these polymers are biocompatible.

In various embodiments, the first and second hydrophilic polymers are crosslinked via a click chemistry reaction. As defined herein, a click chemistry reaction is a reaction in which crosslinking of first and second reactants (i.e., the first and second hydrophilic polymers) occurs immediately upon contact with each other, while generating minimal and biocompatible byproducts and while being able to proceed in the presence of water.

In various embodiments, the first hydrophilic polymer is functionalized with a plurality of first functional groups, the second hydrophilic polymer is functionalized with a plurality of second functional groups, and the first and second functional groups react and form covalent bonds upon a change in pH, such that the first and second hydrophilic polymers react and crosslink with one another. Although particular embodiments are described herein in which the first and second functional groups react to form amide bonds upon a change in pH, it should be understood that the present disclosure is not limited to the same.

In various embodiments, the medical composition is a free-flowing composition that contains the first and second hydrophilic polymers, for example, a free-flowing dry composition in the form of a powder comprising the first and second polymers or a free-flowing liquid composition comprising the first and second polymers, among others. The medical composition is combined with a second free-flowing composition that is adapted to form a pH environment that results in crosslinking of the first and second polymers, for example, a buffer solution, such that a mixture is formed that has a pH value that causes crosslinking between the first and second hydrophilic polymers. In various embodiments, crosslinking occurs at a rate such that the mixture quickly becomes a non-free-flowing gel, for example, in less than ten minutes, preferably in less than five minutes, at body temperature.

In embodiments, the pH value that causes crosslinking between the first and second hydrophilic polymers ranges from 7 to 9.

In some embodiments, the free-flowing composition that contains the first and second hydrophilic polymers has a pH that ranges from 4 to 5. In some embodiments, the second free-flowing composition is a buffer solution having a pH that ranges from 9 to 10. In some of these embodiments, the resulting mixture will have a pH of 7 to 8.

In some embodiments, the first functional groups comprise succinimidyl groups and the second functional groups comprise amine groups.

Hydrophilic polymers comprising succinimidyl groups can be formed from polymers that comprise hydroxyl groups, among others.

Although embodiments will now be described in which a multi-arm hydrophilic polymer having arms with terminal hydroxyl groups in converted into a multi-arm polymer having arms with terminal succinimidyl groups, it will be understood that a variety of other polymers having hydroxyl groups, including linear polymers and branched polymers, among others, can be converted in an analogous fashion.

Turning now to FIG. 1, a multi-arm polymer 100 having a core 102 and plurality of hydrophilic polymer arms 104 extending from the core 102, each hydrophilic polymer arm 104 terminated in a hydroxyl group 106, is used to produce a multi-arm hydrophilic polymer 110 that comprises the core 102 and plurality of hydrophilic polymer arms 104, each hydrophilic polymer arm 104 terminated in a succinimidyl group 108.

Figure 2:
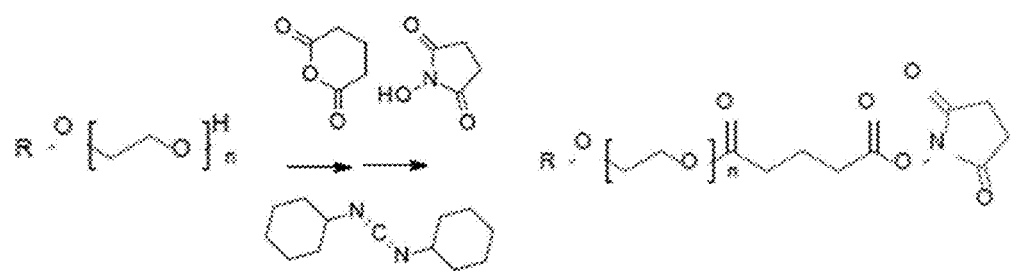
FIG. 2 is a schematic illustration of a method of making a hydrophilic PEG polymer that is functionalized with a plurality of succinimidyl end groups from a PEG polymer that contains a plurality of hydroxyl end groups, in accordance with an embodiment of the present disclosure.

In one particular embodiment illustrated schematically in FIG. 2, a multi-arm polymer having a core R and a plurality hydroxyl terminated polyethylene oxide arms (i.e., where n is an integer of 2 or more) is reacted with a cyclic anhydride such as glutaric anhydride, succinic anhydride, malonic anhydride, etc. (glutaric anhydride is shown) to form a reaction product (not shown) in the form of a multi-arm polymer that comprises the core and the plurality of polymer arms, which polymer arms are terminated in a moiety that comprises a carboxylic acid group and a hydrolysable ester group positioned between the carboxylic acid group and the polymer arm.

Subsequently, this reaction product is treated with a coupling agent (e.g., a carbodiimide coupling agent such as N,N'-dicyclohexylcarbodiimide (DCC) or another coupling agent) and N-hydroxysuccinimide (NHS), to yield polymer arms terminating in moiety that comprises a hydrolysable ester group and a succinimide ester group, in particular polymer arms comprising succinimidyl glutarate end groups.

Various hydrophilic polymers comprising amine groups, specifically, primary amine groups, are available commercially and include chitosan (a mucoadhesive, highly swellable polymer having antimicrobial properties), lysine-containing oligopeptides and proteins including lysine polypeptides containing 2, 3, 4, 5, 6, 7, 8, 9, 10 or more lysine units. The primary amine groups that are found on theses compounds make them eligible for participation in a variety chemical reactions, including covalent crosslinking reactions with other functional groups (e.g., succinimidyl groups), which can improve cohesion to tissue and duration.

Hydrophilic polymers comprising amine groups can also be formed from other polymers. For example, glycosaminoglycans (e.g., chitin, hyaluronan, chondroitin, dermatan, heparin/heparan, heparosan, keratan, etc.), which have acetylated amino sugar units (e.g., N-acetylglucosamine, N-acetylgalactosamine units, etc.), may be subjected to a suitable treatment (e.g., with a base) to convert the acetylated amino sugar units to amino sugar units (e.g., glucosamine or galactosamine units). For example, chitin, which is a polymer of N-acetylglucosamine units, may be deacetylated in this fashion to form chitosan, which is a polymer of glucosamine units (and typically unconverted N-acetylglucosamine units as well, depending on the degree of deacetylation).

Figure 3:
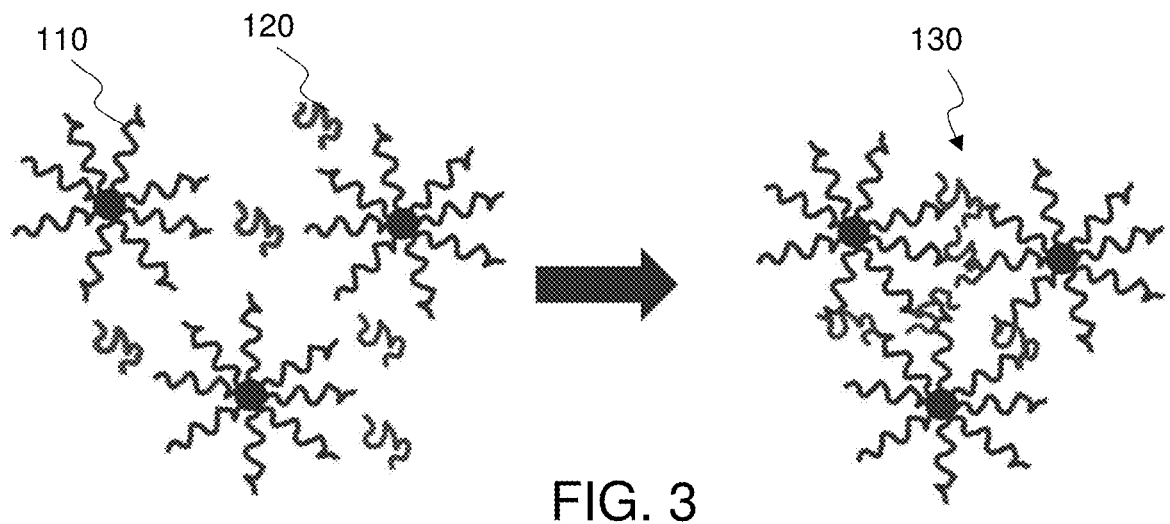
FIG. 3 is a schematic illustration of a crosslinking reaction between a reactive hydrophilic polymer like that of FIG. 1 and an additional hydrophilic polymer, in accordance with an embodiment of the present disclosure.

Once obtained, a first hydrophilic polymer functionalized with a plurality of succinimidyl groups (e.g., a succinimidyl-terminated multi-arm hydrophilic polymer such as succinimidyl-terminated multi-arm PEG) can be reacted with a second hydrophilic polymer functionalized with a plurality of amine groups (e.g., a polysaccharide having glucosamine or galactosamine units such as chitosan) via an amide coupling reaction in which the succinimidyl groups react with the amine groups to form amide linkages, thereby crosslinking the first and second hydrophilic polymers. Such a reaction is shown schematically in FIG. 3, wherein succinimidyl terminated multi-arm hydrophilic polymer 110 is crosslinked with a polyamine 120 to form a crosslinked product 130 (e.g., a non-free-flowing gel). In embodiments, the first and second hydrophilic polymers can be provided in a pH 4-5 solution and mixed with a pH 9-10 buffer solution to yield an overall pH of 7-8, and which pH the first and second hydrophilic polymers quickly react and form a cohesive gel.

It is noted that the rate of reaction between succinimidyl groups and primary amine groups is very low at acidic pH (e.g., a pH ranging from 4 to 5) but increases dramatically at neutral to alkaline (e.g., a pH ranging from 7 to 8 or more). This allows a first composition containing a first hydrophilic polymer comprising succinimidyl groups and a second hydrophilic polymer comprising a plurality of amino groups and having a pH of 4 to 5 to be applied to tissue in coordination with a second composition that is a free-flowing liquid composition (e.g., a buffer solution having a pH ranging from 9 to 10) that raises the pH of the first liquid composition when the second composition is mixed with the first composition. This mixing causes the pH environment of the first and second hydrophilic polymers to increase (e.g., to a pH ranging from 7 to 8), resulting in rapid chemical reaction (and thus crosslinking) between the first and second polymers, in this case an amide coupling reaction. The resulting composition is a crosslinked non-free-flowing gel that can act, for example, as a protective barrier over the tissue. The non-free-flowing gel may be formed in less than 10 minutes, preferably less than 5 minutes, at body temperature, in some embodiments.

In some embodiments, the first composition is a free-flowing liquid composition that comprises the first and second hydrophilic polymers and has a pH in a range of 4 to 5. In these embodiments, the first and second compositions may be applied to the tissue independently (i.e., by applying the first composition followed by the second composition, or vice versa) or the first and second compositions may be mixed and applied to the tissue.

In some embodiments, the first composition is a free-flowing dry composition (e.g., a powder) comprising the first and second hydrophilic polymers. In these embodiments, the first and second compositions may be applied to the tissue independently or the first and second compositions may be mixed and applied to the tissue. In some embodiments, the first composition is initially applied to the tissue, followed by application of the second composition to the tissue. In some embodiments, the first composition is initially applied to the tissue, followed by application of a free-flowing liquid composition having a pH ranging from 4 to 5 (thereby ensuring that the first and second hydrophilic polymers are solubilized), followed by application of the second composition to the tissue.

More generally, (a) first composition that is a free-flowing composition containing a first polymer comprising first functional groups and a second polymer comprising second functional groups and having a pH wherein a rate of reaction between the first and second functional groups is very low (including reaction rates that are so low as to be non-measurable) may be mixed with (b) a free-flowing second liquid composition that, when mixed with the first liquid composition, changes the pH of the first liquid composition to a pH value where a rate of reaction between the first and second functional groups increases rapidly, resulting in crosslinking between the first and second hydrophilic polymers. In some embodiments, the first composition is a free-flowing liquid composition that comprises the first and second hydrophilic polymers. In some embodiments, the first composition is a free-flowing dry composition (e.g., a powder) comprising the first and second hydrophilic polymers. As above, in either case the crosslinked composition is a non-free-flowing gel that can act, for example, as a protective barrier over the tissue, and the non-free-flowing gel may be formed in less than 10 minutes, preferably less than five minutes, at body temperature, in some embodiments.

In various embodiments, the present disclosure pertains to medical procedures in which protective barriers are formed on bodily tissues.

In some embodiments, a first free-flowing composition as described herein (e.g., a first free-flowing liquid composition comprising first and second hydrophilic polymers as described herein or a first free-flowing powder composition comprising first and second hydrophilic polymers as described herein) may be applied to tissue followed by application of a second free-flowing liquid composition as described herein (e.g., a buffer solution having a pH ranging from 9 to 10) onto the first free-flowing composition, after which the first and second liquid compositions passively mix (e.g., via diffusion).

In embodiments where a first free-flowing powder composition comprising first and second hydrophilic polymers as described herein is applied to tissue followed by application of a second free-flowing liquid composition as described herein (e.g., a buffer solution having a pH ranging from 9 to 10), a third free-flowing liquid composition (e.g., having pH ranging from 4 to 5) may be applied after to the first free-flowing powder composition and prior to the second free-flowing liquid composition.

Alternatively, a second free-flowing composition as described herein may be applied to tissue, followed by application of a first free-flowing liquid composition as described herein, In some embodiments, the first and second compositions may be mixed with one another at the time of application to tissue, for example, using a suitable delivery device that mixes the first and second compositions.

Where the first and second free-flowing compositions are free-flowing liquid compositions, the first free-flowing liquid composition and the second free-flowing liquid composition may be mixed in a variety of ratios ranging for example, from 10:1 and 1:10, from 5:1 to 1:5, or from 2:1 to 1:2, among other possibilities.

Tissues to which the first and second compositions may be applied include gastrointestinal tissue (e.g., the large intestine, colon and/or the esophagus).

In some embodiments, the first and second compositions are applied to the tissue endoscopically.

In various embodiments, systems are provided which include (a) a first reservoir that contains a first free-flowing composition comprising first and second hydrophilic polymers as described herein (e.g., a free-flowing liquid composition that comprises first and second hydrophilic polymers and has a pH in a range of 4 to 5, or a free-flowing dry composition comprising first and second hydrophilic polymers) and (b) a second reservoir that contains (i) a second free-flowing liquid composition as described herein that raises the pH of the first composition when the second composition is mixed with the first composition (e.g., a buffer solution having a pH ranging from 9 to 10) or (ii) a dry composition to which a suitable diluent can be added (e.g., water for injection, saline, etc.) to form such a second free-flowing liquid composition.

In some embodiments, the system will further include one or more delivery devices for delivering the first and second free-flowing compositions to a subject. For example, the system may include a delivery device that comprises a first reservoir that contains the first free-flowing composition and a second reservoir that contains the second free-flowing liquid composition. During operation, the first and second free-flowing compositions are dispensed from the first and second reservoirs, whereupon the first and second free-flowing compositions interact to form a non-free-flowing gel.

In some embodiments, the device may further comprise a cannula or catheter tube that is configured to receive first and second free-flowing compositions from the first and second reservoirs.

During operation, the first and second free-flowing liquid compositions are dispensed from the first and second reservoirs such that the first and second free-flowing liquid compositions are administered onto or into tissue of a subject, during and/or after which the first and second free-flowing liquid compositions crosslink to form a hydrogel.

In addition to the first and second hydrophilic polymers, first free-flowing compositions as described herein may further comprise therapeutic agents, imaging agents, or other additional agents.

In addition to the pH buffer, second free-flowing liquid compositions as described herein may further comprise therapeutic agents, imaging agents, or other additional agents.

Examples of therapeutic agents include antimicrobial agents, including antibacterial agents, antifungal agents, antiviral agents, and antiparasitic agents, and growth factors including cancer growth factors, interferon gamma, interleukin 12, interleukin 17, and interleukin 2, among others.

Examples of imaging agents include fluorescent dyes, magnetic resonance imaging (MRI) contrast agents, ultrasound contrast agents, radiocontrast agents and near-infrared (NIR) imaging contrast agents.

In some embodiments, the first and/or second hydrophilic polymer may comprise radiopaque functional groups such as iodine-containing groups.

In some embodiments, the present disclosure pertains to kits for applying the compositions described herein to bodily tissue, for example, in order to form protective barriers on bodily tissue.

In some embodiments, the kits may comprise a reservoir containing a first composition as described herein, and a reservoir comprising a second composition as described herein.

In some embodiments, the kits may comprise a reservoir containing first and second hydrophilic polymers in powder form. In some embodiments, the kits may further include a reservoir containing a liquid composition (e.g., water, saline, or a buffer such as a pH 4-5 buffer) which, at the time of administration to a patient, can be mixed with the first and second hydrophilic polymers in powder form to form a first free-flowing liquid composition as described herein. Such embodiments may be useful in cases where the first and/or second hydrophilic polymers are not sufficiently stable when combined together in liquid form.

Alternatively or in addition, in some embodiments, the kits may comprise a reservoir containing a second free-flowing liquid composition as described herein (e.g., a buffer solution such as a pH 9-10 buffer solution) or a powder which may, at the time of administration to a patient, be mixed with a liquid composition (e.g., water, saline, etc.) to form a second free-flowing liquid composition as described herein (e.g., a buffer solution such as a pH 9-10 buffer solution).

In some embodiments, the kits may comprise a first reservoir containing a first hydrophilic polymer as described herein, a second reservoir comprising a second hydrophilic polymer as described herein, and a third reservoir comprising a second free-flowing liquid composition as described herein or a powder precursor thereof. At a time of delivery to a patient, the first and second hydrophilic polymers may be combined to form a first free-flowing liquid composition as described herein which can then be administered to a patient along with the second free-flowing liquid composition. Such embodiments may be useful in cases where the first and/or second hydrophilic polymers are not sufficiently stable when combined together in solid or liquid form.

For example, in one embodiment, the first reservoir may contain succinyl-derivatized PEG in powder form as the first hydrophilic polymer and the second reservoir may contain a free-flowing liquid composition that comprises chitosan. At a time of delivery to a patient, the free-flowing liquid composition that comprises chitosan may be mixed with the succinyl-derivatized PEG in powder (e.g., by removing the free-flowing liquid composition that comprises chitosan from the second reservoir and adding it to the first reservoir, by breaking a seal that separates the free-flowing liquid composition that comprises chitosan in the second reservoir from the succinyl-derivatized PEG in powder in the first reservoir, etc.), thereby forming a first free-flowing liquid composition as described herein, which can then be administered to a patient along with the second free-flowing liquid composition as described herein.

In some embodiments, the kits may comprises a delivery device. Alternatively or in addition, the kits may comprise a cannula or catheter tube.

Example 1

This example utilizes amine functional groups from chitosan and, optionally, from a lysine polypeptide (trilysine), and succinimide functional groups from succinimide terminated PEG, that react with each other when at an elevated pH (7-9 pH) is achieved but not at a lower pH (5-6 pH). This reaction follows Michaels addition chemistry and it is at this elevated pH that the amine and succinimide groups react and form a cohesive gel. The specific succinimide terminated PEG compound used in this example is 8-arm PEG with succinimidyl glutarate end groups (PEG-SG) available as one of the system components in SpaceOAR®, available through Augmenix. The specific chitosan used can may be, for example, high (e.g., 310000-375000 Da) and/or low (e.g., 50,000-190,000 Da) molecular weight chitosan, which may be of shrimp shell origin, available from Sigma-Aldrich.

A first free-flowing liquid composition (Part A) is mixed with a second free-flowing liquid composition (Part B), thereby elevating the pH of the admixture to a pH of 7.5. Although the compositions that are mixed are initially free flowing liquid compositions, after mixing a gelled material is formed that is not free flowing. Formulations that may be employed include those presented below in Tables 1-3.

TABLE 1

| Part A | Part B |
|---|---|
| 5 mL low mol. wt. chitosan (2-3% solids) in 1% acetic acid in water (AA/H$_2$O), combined with 0.5 g PEG-SG, and 0.5 mL pH 4 (AA/H$_2$O) | 6 mL pH 9 buffer |

TABLE 2

| Part A | Part B |
|---|---|
| 5 mL low mol. wt. chitosan (2-3% solids) in 1% AA/H$_2$O, combined with 0.5 mL pH 4 (AA/H$_2$O) 0.5 g PEG-SG and 1 mL Triysine | 6 mL pH 9 buffer |

TABLE 3

| Part A | Part B |
|---|---|
| 5 mL low mol. wt. chitosan (2-3% solids) in 1% AA/H$_2$O, combined with 0.5 mL pH 4 (AA/H$_2$O) 0.5 g PEG-SG and 0.5 mL Trilysine | 6 mL pH 9 buffer |

Example 2

This example also utilizes amine functional groups from chitosan and succinimide functional groups from succinimide terminated PEG. In this example, a free-flowing composition is formed by mixing the chitosan and PEG, for example, in a volume ratio ranging from 1:1 to 1:0.5 (Chitosan:PEG).

In alternative embodiments, the chitosan portion of the mixture may comprise modified chitosan in addition to or in place of the chitosan. Examples of modified chitosan include carboxymethylchitosan crosslinked with chitosan (high and/or low molecular weight), thiolated chitosan, and thiol-chitosan-PEG copolymer.

Such mixtures may be solubilized in pH 4 solution, after which crosslinking is effected by combination with a pH 9 buffer.

The invention claimed is:

1. A medical composition comprising:
   (a) a first hydrophilic polymer functionalized with a plurality of first functional groups that comprise succinimidyl groups; and
   (b) a second hydrophilic polymer functionalized with a plurality of second functional groups that comprise primary amine groups,
   wherein the first and second functional groups are selected to react and form covalent bonds upon a change in conditions such that the first and second hydrophilic polymers crosslink with one another, wherein the composition is a first composition that comprises a mixture of the first and second hydrophilic polymers, wherein the second polymer is a polysaccharide, wherein said change in conditions is a change in pH, and wherein the first and second hydrophilic polymers crosslink with one another at a rate such that the mixture becomes a non-free-flowing gel in less than 5 minutes at body temperature.

2. The medical composition of claim 1, wherein the first and second hydrophilic polymers crosslink with one another when a pH of an environment surrounding the mixture of the first and second hydrophilic polymers has a pH value ranging from 7 to 9.

3. The medical composition of claim 1, wherein the succinimidyl groups are linked to the first hydrophilic polymer by a hydrolysable linkages.

4. The medical composition of claim 1, wherein the first hydrophilic polymer is a multi-arm hydrophilic synthetic polymer having arms that comprise said succinimidyl groups.

5. A kit for forming a protective barrier on bodily tissue comprising:
   (a) a first hydrophilic polymer functionalized with a plurality of first functional groups that comprise succinimidyl groups; and
   (b) a second hydrophilic polymer functionalized with a plurality of second functional groups that comprise primary amine groups,
   wherein the second hydrophilic polymer is a polysaccharide, wherein the first and second functional groups are selected to react and form covalent bonds upon a change in a change in pH, and wherein the first and second functional groups react and form covalent bonds when a pH of an environment surrounding a mixture of the first and second hydrophilic polymers is changed from a first pH value to a second pH value that differs from the first pH value.

6. The kit of claim 5, wherein the kit comprises (a) a first reservoir containing a first free- flowing liquid composition having said first pH value and comprising the first and second hydrophilic polymers, (b) a first reservoir containing a dry composition that comprises the first and second hydrophilic polymers and is adapted to form a first free-flowing liquid composition having said first pH value and comprising the first and second hydrophilic polymers, (c) a first reservoir containing a dry composition that comprises the first hydrophilic polymer and a second reservoir containing a free flowing liquid composition that comprises the second hydrophilic polymer, wherein when contents of the first and second reservoir are mixed, a first free-flowing liquid composition is formed having said first pH and comprising the first and second hydrophilic polymers, or (d) a first reservoir containing a first free-flowing dry composition comprising the first and second hydrophilic polymers that is configured to be propelled as a dry composition onto tissue.

7. The kit of claim 6, wherein the kit further comprises an additional reservoir containing (a) a second free-flowing liquid buffer composition or (b) a powder that is configured to form a second free-flowing liquid buffer composition upon addition of a suitable diluent.

8. The medical composition of claim 1, wherein the second hydrophilic polymer is chitosan.

9. The medical composition of claim 1, wherein the first hydrophilic polymer is a multi-arm hydrophilic synthetic polymer having arms that comprise said succinimidyl groups and the second hydrophilic polymer is chitosan.

* * * * *